United States Patent [19]

Romanauskas

[11] Patent Number: 4,756,883

[45] Date of Patent: Jul. 12, 1988

[54] ANALYSIS DEVICE

[75] Inventor: William A. Romanauskas, Southbury, Conn.

[73] Assignee: E. I. Du Pont de Nemours and Company, Wilmington, Del.

[21] Appl. No.: 908,045

[22] Filed: Sep. 16, 1986

[51] Int. Cl.[4] .................................................. G01N 21/07
[52] U.S. Cl. ......................................... 422/72; 436/45; 356/246
[58] Field of Search .................... 422/72, 64; 436/45; 356/246, 428

[56] References Cited

U.S. PATENT DOCUMENTS

| | | | |
|---|---|---|---|
| 3,555,284 | 1/1971 | Anderson | 250/218 |
| 3,744,975 | 7/1973 | Mailen | 422/72 |
| 3,798,459 | 3/1974 | Anderson | 250/218 |
| 3,873,217 | 3/1975 | Anderson et al. | 356/246 |
| 4,123,173 | 10/1978 | Bullock et al. | 356/246 |
| 4,154,793 | 5/1979 | Grugan | 422/72 |
| 4,244,916 | 1/1981 | Grugan | 422/72 |
| 4,284,602 | 8/1981 | Kelton et al. | 422/72 |
| 4,387,164 | 6/1983 | Hevey et al. | 436/45 |
| 4,469,793 | 9/1984 | Grugan | 436/45 |
| 4,470,954 | 9/1984 | Chiknas | 422/72 |
| 4,588,555 | 5/1986 | Provonchee | 436/45 |

FOREIGN PATENT DOCUMENTS

| | | |
|---|---|---|
| 1152353 | 8/1983 | Canada ................... 422/72 |
| 0039825 | 4/1981 | European Pat. Off. . |
| 0062907 | 4/1982 | European Pat. Off. . |
| 0052769 | 6/1982 | European Pat. Off. . |
| 0052770 | 6/1982 | European Pat. Off. . |
| 2529245 | 7/1977 | Fed. Rep. of Germany . |
| 2506015 | 5/1981 | France . |

OTHER PUBLICATIONS

Analytical Chemistry, vol. 45, No. 3, Mar. 1973, pp. 327A–340A, US: C. D. Scott et al.: "A Miniature Fast Analyzer System", p. 329A, right-hand column, last paragraph–p. 330A, left-hand column; FIG. 2.

Primary Examiner—Michael S. Marcus

[57] ABSTRACT

A centrifugal analysis device is provided in which a plastic rotor has peripheral cells each containing a reagent. The rotor is configured such that sample fluid within a central receptacle is equally dispensed to each of the peripheral cells. An outlet orifice is positioned at a radial distance greater than the inlet orifice to each cell such that each cell is permitted (1) to be completely filled with fluid and (2) simultaneously such that all reactions take place at the same beginning point.

13 Claims, 1 Drawing Sheet

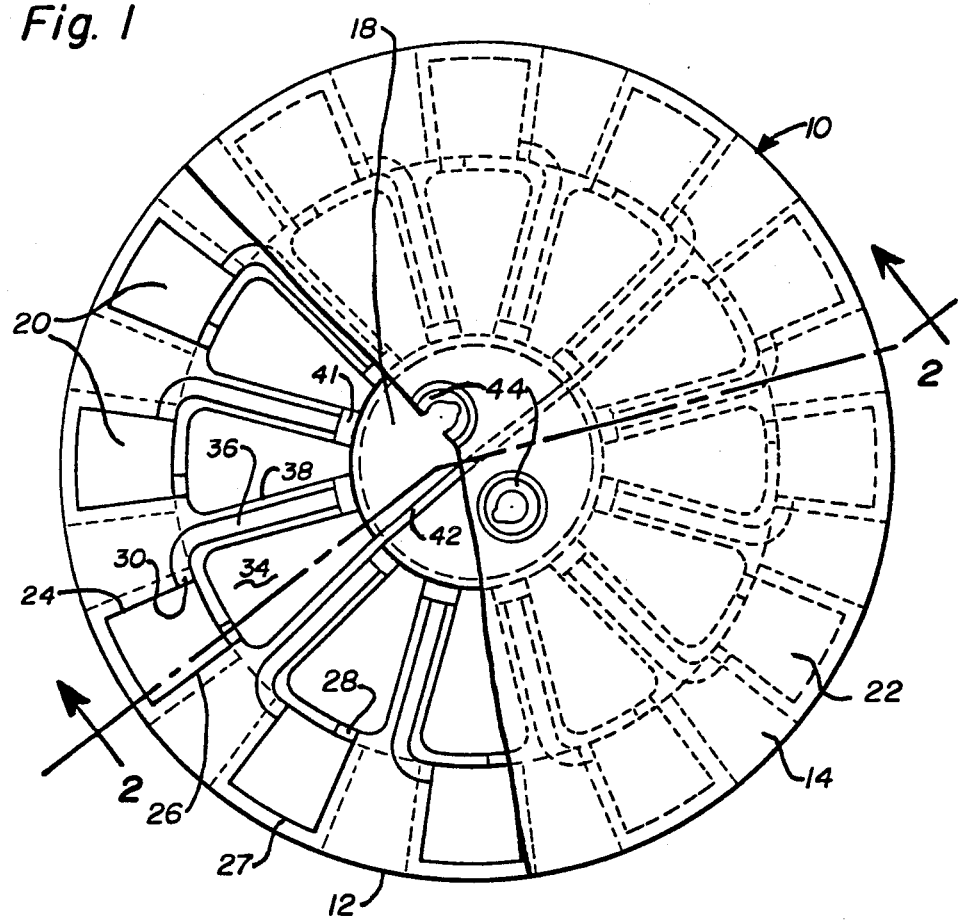

4,756,883

ANALYSIS DEVICE

CROSS REFERENCE TO RELATED APPLICATIONS

The invention described herein is related to an invention described in an application U.S. Ser. No. 908,046, filed Sept. 16, 1986 by W. A. Romanauskus and entitled "Analysis Device".

FIELD OF THE INVENTION

This invention relates to a centrifugal device for analyzing liquid samples.

BACKGROUND OF THE INVENTION

Many automatic analysis devices are known in which one or more liquid samples are introduced into a reagent-carrying rotor. Rotation of the rotor causes the displacement of the liquids to be analyzed towards the cells containing the reagents. Changes of the optical characteristics in the cells where the reaction takes place (changes in opacity, light absorption, color, refraction index, etc.) are measured. In this way, a series of measurements can be obtained which make possible the analysis of one or more samples.

In fact, older devices utilized cells mounted in series or in a descending series on a common support (sample cells, reagent cells, reaction cells) in which the sample moves from one cell to the other by any appropriate means, for example, by gravity. Several reagents and successive reaction cells can be utilized in this way. The proposal was then made to radially arrange these supports on a rotor to make use of the centrifugal force for the purpose of displacing the liquids (samples and possibly reagents) but each elementary support remained independent.

Rotors were conceived on which a series of supports with one or more radial series of cells were placed (see European application Nos. 0 052 769 and 0 052 770 Boehringer Mannhein, for example). Also rotors without separate supports were used but provided for the introduction of the common central inlet followed by separated radial cells (see, for example, U.S. Pat. Nos. 3,744,975 Mailen and 3,798,459 Anderson). But most of these devices often only provided mediocre measurements as a result of nonuniformity of the dosages.

In one form of such centrifugal analyzers, dry reagents are held in small disposable cells located peripherally in a small disposable plastic rotor. The cells have optically clear top and bottom windows. Previously conditioned samples (typically of body fluids such as plasma or urine) are introduced into a receptacle in the center of the rotor. Since many of the reactions with the reagents are time dependent, it is required that the body fluids do not reach the reagents until desired. Centrifugal force is used to transfer the body fluids to the peripheral cells for analysis. To accomplish this transfer, the rotor is accelerated causing the body fluids to move centrifugally out to the cells and reagents. After a prescribed time the color changes are read optically to determine the results of the test. Since many cells (each with different reagents to perform a separate analysis) can be positioned in each rotor, the result is a fairly complete chemistry of the body fluid in a compact unit in a relatively short period of time.

Typical of these rotors are those described in U.S. Pat. Nos. 4,123,173, 3,555,284 and 4,387,164. While quite satisfactory for their intended purposes these rotors do not fulfill the need that exists for a small disposable rotor that is capable of accurately providing many tests on a single sample. Disposable rotors of this type are described in a series of patents issued to Guigan. Typical of these patents are U.S. patent application Ser. No. 626,749 filed July 2, 1984 and U.S. Pat. No. 4,154,793. These rotors are comprised of two disk-like rigid plastic pieces secured together to form a closed rotor. The lower disk has a central hub for mounting on a rotor drive shaft and comprises a flat disk having a central receptacle and a plurality of peripheral cells formed therein. Each cell is separated from an adjacent cell by a raised radial ridge which forms sectors for each cell. A radial groove of capillary thickness dimensions extends from the central receptacle formed in the lower disk to the center, radially inner portion of each cell.

The top disk has a flat lower surface which is sealed to the radial ridges and periphery of the lower disk so as to provide the closed rotor. The rotor thus defines a plurality of small sectors each with a slit of capillary dimensions communicating with each cell from the central cavity. This rotor is a disposable unit adapted to receive a patient sample, through an opening in the center portion of the upper disk, which is retained in the central receptacle. The sample when subjected to centrifugal force is preferentially driven by the combined action of centrifugal force and capillary action to each sector to fill each cell. Air escapes from each cell through the groove formed in the lower disk.

One problem inherent in the Guigan design is that different chemistries, different dilutions or different fluids are necessary; therefore, more than one central well is required. This is typically accomplished by placing a baffle in the central receptacle. Without the baffle all cells are subjected to the same pressure. With the baffle in the central cavity, due to acceleration, the cells nearest the leading edge of the baffle tend to be filled first. Also, it is sometimes difficult to fill all of the cells completely since the groove tends to become filled with liquid trying to exit the central receptacle under centrifugal force. This can result in filling differences and difficulty of completely filling a particular cell with fluid from the central receptacle.

SUMMARY OF THE INVENTION

Many of these problems of the prior art centrifugal devices are solved by applicant's invention of a device, which improves over the conventional devices, having a rotor, an axis of rotation, a central receptacle and a plurality of peripheral cells, with each cell having two walls for optical measurement, being adapted to hold a reagent in fluid communication with the central receptacle, and having leading and trailing walls or wall portions when the rotor is rotated. Applicant's improvement provides fluid communication between the cells and the central receptacle by an inlet orifice for each cell disposed between the cell and the central receptacle, and each cell being provided with an outlet orifice communicating with the central receptacle from a point in the cell at a greater radial distance from the axis of rotation than the inlet orifice. The inlet orifice is located at the trailing wall portion of the cell and the outlet orifice is located at the leading wall portion of the cell. This permits the complete filling of the cell without the fluid from the central receptacle interfering with the airbleed from the cells. Each outlet orifice is provided by a septum defining a passage extending radially inward into the central receptacle, whereby adjacent septa define wells for each cell extending into the central receptacle. The inlet and outlet orifices are capillary sized, have hydrophobic surfaces to retain liquid in the cell after filling, and prevent premature filling. Each orifice is located in the top portion of the cell so that liquid introduced into the central receptacle does not interfere therewith.

The rotor preferably comprises top and bottom pieces, the bottom piece having vertical partitions defining the cells and central receptacle, the orifices being defined by grooves formed in the partitions on the one hand and a lower surface of the top piece or lid on the other. The rotor may include a baffle dividing the central receptacle in two. With this arrangement, each cell is completely, accurately and rapidly filled without interference from the fluid or liquid in the central receptacle. The outlet orifice is free of liquid and the cell full of liquid. In this way, the compression of air within the cell is limited to the pressure drop in the outlet orifice which, being filled only with air, is relatively low. The wells meter the fluid flow to cells and facilitate their simultaneous fillings.

BRIEF DESCRIPTION OF THE DRAWINGS

The invention may be more fully understood from the following detailed description thereof taken in connection with accompanying drawings which form a part of this application and in which:

FIG. 1 is a plan view partially cut away of a rotor constructed in accordance with this invention; and FIG. 2 is a cross-sectional view of the rotor taken along the section lines 2—2 of FIG. 1.

DESCRIPTION OF THE PREFERRED EMBODIMENT

With reference to FIGS. 1 and 2 there may be seen a centrifugal analysis device constructed in accordance with this invention in the form of a small, plastic disposable rotor. The plastic may be any of those suitably used for this purpose in which the plastic is relatively rigid and nonreactive with the reagents typically used in the analysis of body fluids. Plastics suitable for this purpose include: polymethylmethacrylate, which is preferred, polycarbonate, polystyrene, and ionomer resin. Such plastics preferably are heat sealable or sealable by ultrasonic bonding techniques although suitable adhesives may be used for this purpose.

Thus the rotor 10 is seen to be formed of two plastic pieces, a bottom piece 12 and a top piece 14. The bottom piece 12 defines a central receptacle 18 and a plurality of peripheral cells 20. Each of the cells 20 is provided with two flat preferably parallel optical walls 22. Preferably these are the top and bottom walls defining the cell. Each cell 20 also has, when the rotor is rotated in a clockwise sense to effect the transfer of liquid from the central receptacle 18 to the cells 20, a leading wall or wall portion 24 and a trailing wall or wall portion 26, hereafter referred to as a leading wall portion 24 and a trailing wall portion 26. An inlet orifice 28 is provided for each cell 20 and is located in the upper portion of the cell adjacent the trailing wall portion 26 of the cell. Similarly an outlet orifice or airbleed 30 is located in a top end of the leading wall portion 24 of each cell. If rectangular, each cell may be defined by leading and trailing side walls or wall portions 24 and 26, a peripheral outer wall 27 and a peripheral inner wall 29. Alternatively, and preferably the cell may be cylindrical in shape and may be defined by leading and trailing side wall portions.

Each outlet 30 extends radially inward to the central receptacle 18 and is defined by a groove 36 formed in the upper surface of a septum 38 which extends radially inward to the central receptacle 18 to a point beyond which the sample fluid will be located during centrifugation. Each outlet is fully defined by one of the grooves 36 and the lower surface of the top piece 14 of the rotor. The septa 38 of adjacent cells, positioned roughly at the leading wall or wall portion 24 of each cell location, are seen to define a well 34 for each cell. The upper, radially inner portion of each septum 38 is notched as at 41 to permit some fluid communication between the wells. Also, the depth of the central receptacle is limited by a plate 19 so that most sample fluid spills out to the wells 34.

The bottom rotor piece 12 may be provided with a cylindrical mount 40 for mounting the rotor on a rotor drive shaft for rotation. Also a central baffle 42 may extend across the central receptacle 18 to divide it into two separate sections to accommodate different sera or different dilutions of the same sera. Access to these two sections is provided by ports 44 formed in the top rotor piece 14. The rotor itself preferably, as is the case in most plastics, is formed of a hydrophobic material. If not, it may be treated in a known manner so that its surfaces which contact the sera are hydrophobic. It is particularly important that the surfaces of the outlet orifice 30 and inlet orifice 28 be hydrophobic as will be explained below.

In operation, various reagents, preferably in a dry tabletized form, are positioned in the various cells 20. Sample fluids (sera) to be analyzed are introduced through the ports 44 by a pipette or other suitable device. During introduction, the sample fluid is limited to have a volume, such as that typified by the line 46 (FIG. 2), such that the sera does not reach the level of the cell's inlet orifice 28 or outlet groove 36. The sample and the reagents are thus separated. In order to effect an analysis, the rotor is spun in a direction such that the inlet orifices 28 are on the trailing wall portion of each cell (in this case clockwise). This causes the liquid sample to reorient radially such that its border, depicted by the line 48, does not extend radially inward sufficiently to permit fluid to enter the cells through the grooves 36 of the septa 38. Because of the hydrophobic surface on or of the plastic forming the rotor, there will be some pressure required to fill the cells depending upon the diameter of the capillary inlet orifices 28, the surface tension of the liquid and the degree to which the surface is wetted. Similarly, the outlet orifices 30 resist fluid flow. Thus wicking is not a problem; the fluid cannot enter or leave the cells 20 without the application of some force.

Once the rotor speed is sufficient to apply the centrifugal pressure at which the fluid may flow through the capillary inlet orifices 28, flow starts from each well 34 to its adjoining cell 20. This flow will hug the trailing wall portions 26 of the cells 20 due to the coriolis effect. Air will thus be expelled gently toward the outlet 30 and be permitted to escape through the capillary formed by the grooves 36 and top piece or lid 14 to the central portion of the rotor unimpeded by liquid pressure that tends to prevent such escape as occurs in many of the prior art rotors. Wells 34 act to meter the fluid flow to each cell thereby insuring that all cells will be filled at the same time, in spite of the need for a dividing baffle such as 42. After filling, when the rotor comes to rest, the fluid will remain trapped within the cell due to the hydrophobic surfaces of the capillary sized orifices 28 and 30.

This design has the particular advantage in that the sample fluid is trapped in each of the wells 34 such that it has relatively little tendency during acceleration of the rotor to resist acceleration and splash against the baffle 42 thereby causing premature filling of the cell immediately contiguous the baffle. This feature, combined with the fact that the air in each cell is allowed to escape relatively easily without having to oppose fluid attempting to enter the cell, provides a relatively advantageous rotor that permits complete filling of the cells all at precisely the same time thus overcoming many of the disadvantages of the prior art rotors of this type. A compression of air within the cell is limited essentially to the pressure drop within the capillary groove 36 of the outlet orifice which is relatively low.

I claim:

1. In a centrifugal device for analyzing a liquid sample comprising a rotor having an axis of rotation, a central receptacle and a plurality of peripheral cells, each of the cells having two walls for optical measurement, being adapted to hold a reagent, having fluid communication means for providing fluid communication between the cell and the central receptacle, having inner and outer radially spaced wall portions, and having leading and trailing wall portions when the rotor is rotated one direction about the axis of rotation, the improvement wherein the fluid communication means between the cells and the central receptacle is provided by a liquid inlet orifice in the inner wall portion of each of the cells, each of the cells is provided with an air outlet orifice partially in the leading wall portion at a point at a greater radial distance from the axis of rotation than the inlet orifices and substantially spaced from the outer wall portion, and each of the air outlet orifices comprises passage means for passing air from the cells to the central receptacle.

2. A device as set forth in claim 1 wherein each of the inlet orifices is located contiguous the trailing portion of a different one of the cells.

3. A device as set forth in claim 2 wherein each of the outlet orifices is located contiguous the leading portion of a different one of the cells.

4. A device as set forth in claim 3 wherein each of the outlet orifices is defined partially by a septum having a groove extending radially inward into the central receptacle, whereby adjacent septa partially define separate wells for each of the cells extending into the central receptacle to reduce liquid rotation within the central receptacle.

5. A device as set forth in claim 4 wherein the inlet and outlet orifices are capillary sized to retain liquid in the cells after filling.

6. A device as set forth in claim 5 wherein the inlet and outlet orifices are located at a top end of each of the cells.

7. A device as set forth in claim 5 wherein the inlet and outlet orifices have hydrophobic surfaces.

8. A device as set forth in claim 5 wherein the rotor comprises top and bottom pieces, the bottom piece having vertical partitions comprising the leading and trailing wall portions and the septa, the inlet and outlet orifices being defined by grooves formed in the partitions and a lower surface of the top piece.

9. A device as set forth in claim 1 wherein each of the outlet orifices is located contiguous the leading portion of a different one of the cells.

10. A device as set forth in claim 9 wherein each of the outlet orifices is defined partially by a septum having a groove extending radially inward into the central receptacle, whereby adjacent septa partially define separate walls for each of the cells extending into the central receptacle to reduce liquid rotation within the central receptacle.

11. A device as set forth in claim 10 wherein the rotor comprises top and bottom pieces, the bottom piece having vertical partitions comprising the leading and trailing wall portions and the septa, the inlet and outlet orifices being defined by grooves formed in the partitions and a lower surface of the top piece.

12. A device as set forth in claim 1 wherein the air outlet orifices are adjacent the inner wall portions of the cells.

13. A device as set forth in claim 1 wherein the air outlet orifices are immediately adjacent junction points of the inner wall portions and the leading wall portions of the cells.

* * * * *